United States Patent [19]

Saunders et al.

[11] Patent Number: 5,550,060
[45] Date of Patent: Aug. 27, 1996

[54] METHOD AND PROCEDURE FOR PREPARING RED BLOOD FRACTIONS

[75] Inventors: Alexander Saunders, San Carlos; Frank W. Summerfield, Redwood City; Michael A. Zarowitz, San Carlos, all of Calif.

[73] Assignee: Chronomed, Inc., San Carlos, Calif.

[21] Appl. No.: 237,095

[22] Filed: May 3, 1994

Related U.S. Application Data

[63] Continuation-in-part of Ser. No. 970,840, Nov. 3, 1992, abandoned.

[51] Int. Cl.$^6$ .................................................. B01D 21/26
[52] U.S. Cl. ........................... 436/63; 436/50; 436/67; 436/531; 422/72; 422/102; 424/534; 427/2.13; 210/515; 210/516; 210/518
[58] Field of Search ......................... 436/63, 67, 50, 436/531; 422/72, 102, 82.02, 241; 55/386; 424/534; 210/515, 516, 518, 804, 651, 782; 427/2

[56] References Cited

U.S. PATENT DOCUMENTS

| | | | |
|---|---|---|---|
| 3,355,098 | 11/1967 | Farr | 494/35 |
| 3,705,018 | 12/1972 | Taylor | 422/100 |
| 3,850,174 | 11/1974 | Ayres | 604/415 |
| 3,914,985 | 10/1975 | von Behrens | 73/61.4 |
| 4,087,567 | 5/1978 | Sullivan | 427/2 |
| 4,101,422 | 7/1978 | Lamont et al. | 210/515 X |
| 4,189,385 | 2/1980 | Greenspan | 210/136 X |
| 4,210,418 | 7/1980 | Brown et al. | 427/2 X |
| 4,240,796 | 12/1980 | Nakanishi | 427/2 X |
| 4,246,123 | 1/1981 | Cornell et al. | 210/515 X |
| 4,257,886 | 3/1981 | Kessler | 210/516 |
| 4,268,270 | 5/1981 | Gabbay et al. | 436/67 |
| 4,343,793 | 8/1982 | Wissler | 424/534 |
| 4,364,832 | 12/1982 | Ballies | 210/518 |
| 4,372,747 | 2/1983 | Gabbay et al. | 436/67 |
| 4,399,227 | 8/1983 | Niederau et al. | 436/67 |
| 4,416,778 | 11/1983 | Rogers | 210/516 |
| 4,438,204 | 3/1984 | Deeg et al. | 436/67 |
| 4,448,888 | 5/1984 | Bleile et al. | 436/67 |
| 4,463,098 | 7/1984 | Hoberman | 436/67 |
| 4,465,774 | 8/1984 | Huang et al. | 436/15 |
| 4,499,052 | 2/1985 | Fulwyler | 422/52 |
| 4,582,606 | 4/1986 | McCarty | 210/516 |
| 4,647,654 | 3/1987 | Knowles et al. | 530/326 |
| 4,822,745 | 4/1989 | Burns et al. | 436/63 |
| 4,828,716 | 5/1989 | McEwen et al. | 210/740 |

(List continued on next page.)

FOREIGN PATENT DOCUMENTS

| | | |
|---|---|---|
| 0126390 | 11/1984 | European Pat. Off. . |
| 0536658 | 4/1993 | European Pat. Off. . |
| 2555074 | 5/1985 | France . |
| 9217107 | 10/1992 | WIPO . |

OTHER PUBLICATIONS

Nakashima, et al., "Glycated Hemoglobin in Fractionated Erythrocytes," *Clin. Chem.*, 35(6):958–62 (1989).

Saunders, A., "Retrospective Time–Resolved Testing: Model 1—Time–Resolved Glycohemoglobin," *Clin. Chem.* 37(9):1531–33 (1991).

Leif, et al., *Proceedings of the National Academy of Sciences*, 51:520–8 (1964).

*Primary Examiner*—Jill Warden
*Assistant Examiner*—Harold Y. Pyon
*Attorney, Agent, or Firm*—Iver P. Cooper

[57] ABSTRACT

Methods and apparatus for separating red blood cells by density are described. Older red blood cells are more dense than younger ones. Certain changes in the physiology are recorded in changes in hemoglobin or the red blood cells. By assaying different aged red blood cells, one can determine the historical physiological changes over a period of many weeks. Improved separation of red blood cells is accomplished by using rigid capillary tubes having an inner surface which augments the density equilibrium of red blood cells and/or incrementally increasing the centrifugation forces, as well as by chemically treating red blood cells to improve their deformability.

24 Claims, 1 Drawing Sheet

U.S. PATENT DOCUMENTS

| | | | |
|---|---|---|---|
| 4,835,097 | 5/1989 | Saunders | 435/4 |
| 4,861,477 | 8/1989 | Kimura | 210/359 |
| 4,875,364 | 10/1989 | Levine et al. | 73/61.1 |
| 4,921,618 | 5/1990 | Hamlin | 210/780 |
| 4,966,785 | 10/1990 | Springston | 427/39 |
| 5,034,135 | 7/1991 | Fischel | 210/651 |
| 5,039,421 | 8/1991 | Giddings | 210/695 |
| 5,100,564 | 3/1992 | Pall et al. | 210/782 |
| 5,135,719 | 8/1992 | Hillman et al. | 422/101 |

FIG. 1

METHOD AND PROCEDURE FOR PREPARING RED BLOOD FRACTIONS

The experiments performed in this applications were supported in part by the National Institute of Diabetes, Digestive and Kidney Disorders grant number RYDK41597. The United States Government has certain rights to this patent application.

The present application is a continuation in part of application Ser. No. 07/970,840, filed Nov. 3, 1992, and now abandoned, the entire contents of which are hereby incorporated by reference.

FIELD OF THE INVENTION

The invention relates to methods and apparatus for determining the physical condition of a patient over time which is recognizable in red blood cells of different ages taken from a single sample.

BACKGROUND TO THE INVENTION

Blood tests provide useful information but generally only indicate the current status of a patient. Many clinicians have wished for a way to determine the physical condition of a patient in retrospect over a period of time. In a number of diseases such as diabetes, it would be useful to determine the recent changes in health status in a patient and correlate such changes with the patient's own recollection of diet, exercise and medication. However, currently, there are few easily assayed records of physiological changes.

Previous infections have been detectable by the presence of antibodies. However, measuring antibodies is indicative of only a few conditions and generally does not indicate how long it has been since exposure to the antigen unless it is recent enough for IgM antibodies to be present. Metabolic changes in the past are generally not detectable using currently commercially available assays.

During the average 120 days of red blood cell (RBC) life, the RBC are exposed to the entire body and may undergo many changes in response to the body condition.

The most prominent red blood cell component is hemoglobin. Hemoglobin is a molecule which contains a protein portion (globin) and an organometallic portion (heme). This molecule is responsible for delivering oxygen throughout the body. A number of compounds modify hemoglobin, some of which affect its activity. For example, carbon monoxide binds to hemoglobin, making it unable to carry oxygen and thus poisons the molecule. Certain drugs react with hemoglobin to form sulfhemoglobin.

Hemoglobin also may be glycosylated. The resulting molecule, glycohemoglobin, retains its original ability to carry oxygen. There are at least five different forms of glycosylated hemoglobin. For example, hemoglobin may be glycated with glucose, galactose, xylose, other non-metabolized sugars, or with phosphorylated sugars such as ribose-5-phosphate or 5-deoxyxylose. The rate at which hemoglobin is glycosylated to form glycohemoglobin is dependent on the sugar concentration (for example, glucose) in the circulating plasma around the red blood cells at the time of exposure, or on the concentration of sugar accumulating within the red blood cell. It has been proposed to use such measurements as a diagnostic test for diabetes, to determine whether a patient is complying with a particular diet or therapy, and to evaluate the effectiveness of a particular therapy. While the glycation of other proteins causes permanent, cumulative damage, hemoglobin is the short term, readily accessible record of such complications.

Several U.S. Patents involve measuring the proportion of glycohemoglobin to hemoglobin such as 4,399,227, 4,647,654, 4,448,888, 4,438,204, 4,372,747, 4,465,774, 4,268,270 and 4,835,097. The '097 patent teaches the use of this ratio as a clock for determining the age of individual red blood cells and correlating this age with the level of blood sugar or of a drug in the circulation. In recent years glycohemoglobin measurements have attracted attention as a possible indicator of diet in diabetic patients. Nakashima et al, *Clinical Chemistry*, 35(6): 958–62(1989), attempt a correlation with blood sugar at the time the glycohemoglobin sample was taken.

Other chemicals may be measured in red blood cells. Alcohol causes a different sugar molecule to become trapped on the hemoglobin molecule due to the indirect action of alcohol on the normal breakdown of sugar in the red blood cell. The altered hemoglobin contains 5-deoxy-D-xylulose-1-phosphate (DXP) and is called "DXP-hemoglobin." Hoberman, U.S. Pat. No. 4,463,098, has proposed a method for determining the historic record of alcohol consumption or abnormal alcohol in the blood by measuring DXP-hemoglobin. However he does not seek to measure hemoglobin with altered glycosylation from non-alcohol related sources. Hoberman's meaning of "historic record" is of general history averaged over the lifespan of 120 days. He does not seek to provide a detailed, calendarized history of alcohol consumption.

Over time erythrocytes (RBC) slowly change density, and may be separated according to age based on their relative densities, Leif et al, *Biochemistry*, 51:520–28(1964). As erythrocytes age, they lose water without significant loss of solids and therefore become more dense, Leif et al, *Proceedings of the National Academy of Sciences*, 51: 520–8(1964). A number of other biochemical changes also occur in erythrocytes over time which has led to various proposals to assay for the age of erythrocytes. See U.S. Pat. No. 4,835,097. While some successes at separating red blood cells have been published, this technique has suffered from a number of problems which have prevented its general clinical use. Previous methods for ordering red blood cells by density, i.e., by age, have been cumbersome. These methods generally involve carefully preparing density gradients and placing the desired sample on top. A centrifugation step follows and harvesting of cells at each layer completes the process. Tests which correlate density layers with age include gradual loss of enzyme activity and also gradual increase in hemoglobin concentration and loss of cell volume.

The present invention has overcome the deficiencies of prior blood cell ordering techniques by variable speed centrifugation of RBCs in plastic-coated glass capillary tubes and improved treatment of red blood cells for deformability and contrast of density.

Varying speed centrifuge techniques such as Wissler, U.S. Pat. No. 4,343,793, have been used to obtain thrombocytes and leukocytes from blood. The blood is centrifuged at low speed whereby all the red blood cells and the leukocytes are sedimented together while the plasma constituents and the thrombocytes remain in the supernatant. The supernatant rich in thrombocytes and plasma constituent is separated from the plasma constituents by brief centrifugation at a higher speed. Wissler did not seek to order red blood cells by age.

Others have used sequential different speeds of centrifuging for various purposes. Rogers, in U.S. Patent No., used several centrifugal forces for harvesting "neocytes" from whole blood for transfusion. However, Rogers only separated two layer, and neither analyzed nor reported the history of a condition.

Von Behrens, in U.S. Pat. No. 3914,985, conducted a low force centrifuge step, followed by a high force centrifugation in a separate container. Von Behrens measured the relative volume of various blood cell types after the second centrifugation. Although he refers to "harvesting", Von Behrens did not harvest cells for measuring a chemical history, nor did he evaluate the history of a condition from either red blood cells or other types of cells.

Nakashima, supra, used a first, low centrifugal force to transfer cells into a capillary, and followed with a second, greater centrifugal force for separating cells into age fractions. Nakashima achieved varying degrees of success in separating fractions by density, but the methods were not optimized for commercial use. Nakashima did not consider the freshness of the samples, and there was no analysis for correlating harvested fractions with density.

McEwen et al., U.S. Pat. No. 4,828,716, disclose a centrifuge assembly for blood separation into serum or plasma and "cellular component" in which the velocity of the linear actuation of the motor is accomplished by a control computer in accordance with sensors which relate the color and degree of turbidity of the separated fluid. The computer uses the signals produced by the optical sensors to determine when optimal separation of the sample has occurred, and stops the motor when the separation process is complete.

Sullivan, in U.S. Pat. No. 4,087,567, discloses an anticoagulant coating suitable for coating the interior surfaces of a blood collection tube, such as a capillary tube. The coating consists essentially of ethylene diamine tetraacetate held in a matrix of polyvinyl pyrrolidone, both of which are dissolved in a water-alcohol mixture to form a coating solution. This is merely to provide an anticoagulant coating for blood collection tubes.

Burns et al., U.S. Pat. No. 4,822,745, disclose a method for determining the reticulocyte population in a blood sample by determining the average cell size of the blood sample, partitioning the sample by centrifugation through a medium of known density so as to provide a fraction enriched with neocytes, determining the average cell size of the fraction, comparing the average cell size of the sample to the average cell size of the fraction and using the comparison to provide a determination of the population of reticulocytes in the sample. This technique, however, is merely for quantifying the reticulocytes in blood, rather than to separate cohorts of red blood cells by age.

Levine, in European patent application 0 536 658 A1, discloses a method for obtaining differential erythrocyte counts. In this case, a blood sample is centrifuged in a transparent tube containing plastic beads which are selected to include groups of beads wherein each group has a different sharply defined specific gravity, and which are distributed within the range of red cell densities. The beads form spaced narrow bands in the erythrocyte layer, which bands form boundaries between the different cell subset layers. The lengths of the different cell subset layers are measured to quantify the red cell subsets in the patient's blood. This method is for obtaining a record of the historical formation and/or loss of red cells in a patient's blood for as much as the previous 120 days. The markers may be plastic beads, latex spheres, or liposomes or the like. Each type of marker has a sharply defined specific gravity which lies within the range of specific gravity for erythrocytes.

European patent application 0 126 390 discloses a fluid transfer device formed to have a cannula for piercing a stopper and surrounding shroud to guide the cannula during piercing.

Glass capillary tubing has been coated previously using a polymer. Springston, U.S. Pat. No. 4,966,785, discloses a method of coating the interior surfaces of glass capillary columns with a stationary polymer phase to minimize progressive phase loss and diminished efficiency of the polymer coating. This coating is used for increasing the chemical adsorption properties, not for cell separation. This is a well known coating which is used here for cross polymerization. These columns are used for gas chromatography. The criterion for the interior coating is stability of the coating to solvents used for washing. There is no disclosure of using these tubes for centrifugation, and no cells are harvested for measurement.

Ohayon, in French patent 2 555 074, discloses separating blood in a plastic or glass tube in which the interior is coated with a film of a copolymer of vinylpyrrolidone and vinyl acetate. The tube contains micronized styrene polymers carrying on their surface hydrated micronized silica. This tube is for separating coagulated blood into a light phase consisting essentially of serum and a heavy phase formed essentially of cellular and fibrillar materials. The tube disclosed by Ohayon aids in coagulating the blood introduced thereinto within a period of about three minutes rather than about 30 minutes. There is no indication that red blood cells can be separated by density-only that the serum can be rapidly separated from the coagulated solid materials in the blood using the combination of the coated tube and the beads of micronized silica.

A number of techniques, including simple decanting have been tried to separate the red blood cells from the remaining components of the blood after centrifugation. Farr, U.S. Pat. No. 3,355,098, discloses an open plunger tube within which is a plastic flexible small bore tube whose lower end extends through an opening in the piston head. After centrifuging, the plunger tube is inserted into the centrifuge tube. As the head of the plunger is pressed into the centrifuge tube, the air above the serum is released to the atmosphere, and serum can be extracted through the capillary tube without disturbing the solids.

Taylor, U.S. Pat. No. 3,705,018, discloses a plug for sealing a test tube which permits access to the tube for removal of some or all of the contents thereof. A U-shaped flow tube extends removably through a pair of spaced-apart apertures in the plug. Withdrawal of one tube end from one of the apertures and application of a negative or positive pressure forces fluid materials into or out of the test tube.

Ayres, U.S. Pat. No. 3,850,174, discloses an assembly for separation of blood into a light liquid phase of serum or plasma and a heavy phase including means for pushing a piston member downwardly in a container. The piston also acts as a closure, and a pointed tubular member can be used to pierce the piston to provide a passage for conducting the separated light liquid phase from one side of the stopper-piston to the other side thereof.

Rogers, U.S. Pat. No. 4,416,778, discloses a method for preparing neocyte-enriched blood wherein a sample of whole blood is centrifuged at high speed to distribute the blood components in the chamber along a density continuum. The container system used contains two chambers. Near the end of the centrifuge cycle, when the container has slowed to a relatively low speed, a valve is opened to permit communication between the two chambers so that the older, dense blood cells distal to the spin axis flow through the conduit into the other chamber. Thus, the second speed in Rogers is for the purposes of transferring cells form one compartment to another.

None of the above-cited patents describes a process for separating red blood cells into refined, multiple fractions of red blood cells which can be sequentially harvested by age and further analyzed to provide a history of a condition.

SUMMARY OF THE INVENTION

It is an object of the present invention to make a system which will be acceptable as a general analytical system, complete with consistent cell separation based on age and sorting of multiple red blood cell fractions for analysis of other changes which would be indicative of past metabolism. The use of this system for monitoring and diagnosing diabetes or hypoglycemia is particularly preferred. Of course, the system can be used for monitoring other conditions over a period of time.

The present invention accomplishes this goal by a number of improvements over the conventional systems. The modifications fall into four areas: the use of plastic coated rigid glass capillary tubes, the use of multiple centrifugation speeds to provide more refined fractions of red blood cells, use of additives to blood samples to further refine separation of fractions by density centrifugation, and use of a particular technique for sequentially harvesting red blood cell age cohorts. The apparatus particularly useful for the sequential separation step is a suction device for harvesting layers of red blood cells by slowly moving the device through the red blood cell pack. Each of these improvements aids substantially in monitoring diabetes over a period of time for up to 120 days.

Apparatus useful for harvesting red blood cells includes means for solidifying or immobilizing the red blood cells, e.g., by freezing, and extracting the solid fractions with a plunger.

These four improvements act together to make a well ordered array of centrifuged red blood cells which have been separated and packed according to their density and presumably by age. The present invention makes it possible to separate red blood cells into at least three different cohorts by density. Each pack of density-separated red blood cells may then be advantageously harvested according to the invention without mixing different density cohorts of red blood cells. Because the various combinations of these four techniques of the present invention enables consistent separation of red blood cells into age cohorts, the present invention provides an accurate measurement of glycosylated hemoglobin as it pertains to the age of red blood cells. Likewise, the history of other chemical changes may be determined by the method of the present invention if the change leaves a permanent, detectable mark on red blood cells. The present invention is not limited to the combination of all four improvements; it also includes the improvements taken individually, and the the various subcombinations.

Studies performed in connection with the present invention have led to the surprising conclusion that, as blood samples reside in the sample tube after removal from the patient's circulation, they undergo subtle changes which decrease separation into density and, presumably, age fractions. These subtle changes begin within three hours of obtaining a sample. It is therefore an object of the present invention to improve separation of red blood cells into density/age fractions substantially independent of the freshness of the samples. The present invention addresses the practical concern of sample transport from donor site to testing laboratory, particularly with respect to maintaining the reliability of the testing procedure even though the samples are not tested immediately upon receiving samples from the patient.

Even when the samples are not fresh, the method of the present invention provides consistent separation of the red blood cells by age cohorts. The process of the present invention has been found to give consistent separation of red blood cells by density even for samples as old as two weeks when the samples have been preserved under refrigeration. The interior coating or lining of the tubes has been found to be particularly important for samples that have been preserved more than a few hours after collection. Since very few samples are separated immediately after collection, it is essential that the separation procedure provide consistent results for samples that are more than a few hours old.

DETAILED DESCRIPTION OF THE PREFERRED EMBODIMENTS

The separation of red blood cells by age in the present invention depends upon the deformability of the red blood cells as they pass each other in order to reach an equilibrium density under elevated gravitational forces. Deformability of red blood cells is an adaptation for these cells to pass through capillaries in the body when the capillaries are smaller than the red blood cells. This adaptation is a squeezing of the red blood cells and a stretching of the capillary. The present invention takes advantage of the fact that red blood cells may deform as they pass each other under the force of gravity, but augments this effect by supplying a tube lining which also promotes deformation of the cells.

A number of tubes have previously been used to separate blood upon centrifugation. These include, glass, polypropylene, polyethylene and heparin coated capillary glass. For purposes of the present invention, the term "capillary tube" denotes a tube having a length to width ratio that makes fractionation possible. A wide tube requires too much sample for separation to be practical. Conventional glass capillary tubes do not function well to permit adequate separation of red blood cell age cohorts because rigidity of the glass boundary does not augment the deformability of the individual red cells seeking equilibrium density under the hydrodynamic forces of centrifugation. Most plastic capillary tubes lack the structural strength of glass capillary tubes and may bend, collapse or rupture upon centrifugation during high gravitational forces, and are difficult to seal. Plastic tubes which resist such bending or collapse conversely lack the ability to deform the cells and thus do not augment separation of cells by density.

According to the present invention, these problems have been overcome by the use of tubes which have an inner coating or lining of a material that augments the density equilibrium of red blood cells. The only advantage of using rigid capillary tubes such as metal or glass is that rigid tubes do not collapse during centrifugation. What is important for the present invention is the interior lining or coating of the tube, which is required for aiding separation by age. However, tubes made of any material which aids in separation by density can be used, and this tube can be inserted into a rigid holder for strength during centrifugation if required. Any material may be used for the inner coating that augments the density equilibrium of red blood cells, for purposes of the present invention.

"Plastic" for purposes of the present invention is a material which is capable of deformation and return to the previous state. This property has been found to be particularly useful for augmenting the density equilibrium of red blood cells. However, for the purposes of the present invention, it is preferable that the plastic be insoluble in water. Hence, the plastics used in the present invention will be refered to as water-insoluble plastics.

The most preferred inner coating is a water-insoluble plastic that closely mimics the flexibility of the body's capillaries. Of course, tubes made of a water-insoluble plastic which augments separation of cells by density can be used rather than an inner coated tube. In the cases in which the water-insoluble plastic is not sufficiently strong to withstand the forces imposed upon it during centrifugation, the plastic tube can be supported during centrifugation. This support may be an outer rigid tube which surrounds the plastic tube. Alternatively, the tube may be surrounded by water or another liquid for support during centrifugation.

Alternatively, tubes made of a plastic which augments separation of the cells by density can be used when they are supported during centrifugation. This support may be by water or by an outer rigid tube surrounding the plastic tube.

The manner in which the internal surface of the capillary tube is coated will vary depending on the inner coating material used. Generally any suitable coating technique may be used. One such example is dissolving a plastic in a solvent and passing the solution or suspension through the glass capillary tube. Other techniques include extrusion, vapor deposition, blowing an inner coating, in situ polymerization on the glass surface and providing a rigid support for a plastic capillary tube. Alternatively, a plastic/glass composite tube may be manufactured directly. One skilled in the art of coating rigid surfaces will readily appreciate that there are a variety of coating techniques that can be used to provide a tube which will withstand the rigors of centrifugation while having an interior which augments the density equilibrium of red blood cells.

The choice of plastics and rigid support materials may be broad and can easily be determined by simple experimentation. For example, the glass capillary tube may be made of borosilicate glass, soda lime glass, lime glass, flint glass, crown glass, optical glass, lead glass and alumina glass. For the purposes of the present invention, plastics to be used include materials generally based upon synthetic resins or upon modified polymers of natural origin. All of the plastics used in the present invention must have the property of augmenting the density equilibrium of red blood cells. The plastics may be either thermosetting or thermoplastic; the important property of the plastics used in the present invention is that they aid in separating red blood cells by density.

Among the plastics that can be used are polyolefins, including polyethylene and polypropylene; poly vinylaromatics such as polystyrenes; halogenated polymers such as polytetrafluoroethylene and polyvinyl chloride; water-insoluble poly vinylalcohols; polyethyleneglycols and fatty acid esters thereof; polycarbonates; polyesters; synthetic rubbers such as polyisoprene and polybutylene; thermosetting resins such as epoxy resins, phenolics, and urea formaldehyde; polyamides, including nylons; polyacetals; acrylic resins, including acrylic and methacrylic esters and copolymers; ionomer resins; and poly aryl sulfones. The plastic may be a homopolymer, block copolymer, graft copolymer, or any mixture thereof. Of these plastics, polystyrene is the most preferred.

Plasticizers that improve the deformability of the plastics may also augment the deformability of the red blood cells, and thus can be incorporated into materials from which the tubes are constructed. Among the plasticizers that can be used in the plastics to enhance the ability of the plastic to augment the deformability of red blood cells are phthalate esters such as dialkyl phthalates and benzyl phthalates; glycol benzoates; trimellitates such as tri-(2-ethylhexyl) trimellitate and mixed esters of substantially linear heptyl and nonyl alcohols; chlorinated paraffins, hydrocarbons and petroleum products such as partially hydrogenated terphenyls, alkylated naphthalenes, benzylated toluenes and the like; esters of dicarboxylic acid esters such as di-2-ethylhexyl esters of adipic, azelaic and sebacic acids; and polyesters of glycols and predominantly aliphatic dicarboxylic acids.

Of course, one skilled in the art can readily formulate a polymer-plasticizer composition that can be used to augment the separation of red blood cells by density.

Other techniques for imparting a plastic-like surface onto glass may be used provided that the resulting inner surface sufficiently augments red blood cell deformity to allow adequate separation of red blood cells based on age. One such method for doing this is by plasma discharge, a conventional technique and used to treat the surface of medical implants, cell culture apparatus and other surfaces contacting biological materials.

Other materials may be added between the plastic coating and the glass base to facilitate adequate bonding between the two materials. The exposed surface of the plastic layer may be coated with heparin, a chemical reacting with calcium or other suitable means to prevent blood coagulation. Where the blood has already been pretreated to prevent coagulation, this coating is unnecessary. Other compounds may be used to coat the plastic to deliver compounds into the sample or to reduce or enhance certain characteristics of the plastic coating.

A suitable capillary tube is typically a very long, thin tube which is capable of holding blood and which is capable of maintaining layers of red blood cells and plasma in distinct layers until analysis can be carried out on the various fractions. A tube meeting these requirements is usually up to , 75 mm long and up to 2 mm wide. Wider tubes can be used, but they are not generally practical because the size (volume) of the sample required increases too rapidly with increases in the diameter of the tube. Tubes with diameters up to 2.4 mm have been found useful. Tubes of a diameter less than about 1.2 mm are also less effective than slightly wider tubes. The size of the tube is not particularly important, and convenient sizes are commercially available between 100μ to 10 ml. Larger and smaller sizes may be used depending on the quantity of sample available and the amount needed for a particular assay.

Whole blood is withdrawn from the patient and preferably treated to prevent coagulation by any standard means such as heparin, citrate ions, EDTA or other calcium chelating agent, or other agent which blocks platelet aggregation and formation of fibrin. EDTA is the preferred anticoagulant. The blood is then placed in a capillary tube. A funnel shaped or wider head space at the top of the capillary tube may be used to facilitate filling and holding plasma after centrifugation. When whole blood is not treated with anticoagulant, the interior of the capillary tube should be so treated to prevent formation of clots.

The capillary tube is then sealed at the bottom if it had not been sealed before filling. It may be sealed with any suitable material, but the standard clay used for hematocrit capillary tubes is an example of such sealant. The top of the capillary tube may also be sealed but the requirements for sealing are generally less stringent since centrifugal forces do not apply pressure to the blood to cause it to escape at the top of the tube. At least one end of the capillary tube should be readily openable to permit access to the pack of red blood cells. The capillary tubes from one or more samples are then loaded into a centrifuge.

Before loading whole blood into capillaries, the sample may be treated by means intended to improve separation into density layers. Among the separation improvers that may be used are treatments which tend to exaggerate the differences in relative density, and other treatments which improve the deformability of red blood cells. Separation aiding agents include agents which make the plasma component hypotonic with the purpose of swelling the cells which are capable of swelling and becoming less dense. Younger cells have been found more able to swell and thus become less dense.

The second type of treatment which can be applied to the sample involves softening the red blood cell membranes with chemical additives. A taurocholate additive is incorporated in the outer leaf or chlorpromazine into the inner leaf of the lipid bilayer membrane of the red blood cells. In high concentrations, these additives are known to hemolyze red blood cells. In low concentrations, they are found to be useful in augmenting red blood cell deformability. This procedures was originally suggested as a mechanism for improving brain oxygenation when chlorpromazine treatment is used in cerebral arteriosclerosis senility. Thus, when a patient with poor cerebral oxygenation receive chlorpromazine, the patient's brain function improves to a point that the patient becomes self supporting.

Another key feature of the present invention is in the centrifugation of blood filled capillary tubes. Unlike conventional centrifugation at a single high speed, the present invention uses a graduated approach. This approach is believed to allow time for the finer density separation between red blood cells in the sample. This process may be performed by a gradual increase in centrifugal force to achieve optimal age separation of red blood cells. Also important is the centrifugation of whole blood without using an artificial density gradient medium.

In the present invention, three centrifugation steps may be used, with the first step being centrifugation at about 20 to about 200 G for about 5 minutes followed by about 2,000 to about 6,000 G for about twenty minutes followed by greater than about 8,000 G for about five minutes. The lowest forces used enable capillary filling and generally separate RBC from plasma. At this point, a gross separation by density begins. At intermediate centrifugal forces, the cells migrate against a gradient of other cells. An equilibrium is probably reached at intermediate G levels. The highest forces cause tight packing and are used for easier subsequent manipulation. These higher forces may also contribute to differential cell migration if equilibrium has not been achieved. Lesser or greater centrifugal force, with corresponding changes in duration, may also be used.

After centrifugation, the capillary tube is removed from the centrifuge. For the purposes of this application, the upper portion of the capillary tube is the portion which contains the least dense contents. The capillary tube should contain a pack of red blood cells on the bottom with buffy coat (of white blood cells and platelets) and plasma above them. The orientation of the tube is not important as long as good separation and clear fractions are obtained. The plasma may be removed by cutting the capillary tube at the level of the buffy coat. Alternatively, one could insert a tight-fitting plunger into the bottom end of the capillary tube and extrude the plasma out from the top of the capillary tube. Freezing the tube minimizes adherence of the cells to the wall of the capillary tube and prevents carry over. Another method for removing plasma is to pump it off with a suction tube. The same structure may be used for removing portions of the red blood cell pack.

Once the plasma is removed, portions of the red blood cell pack are removed sequentially based on their density. It does not matter whether the cells are removed starting with the most dense, the "oldest", or the least dense, the "youngest". The cells may be harvested by pushing out sequential portions of the red blood cell pack, for example, with a plunger, and washing or cutting off a layer. Examples of this are found in Nakashima, *Clinical Chemistry*, 35(6): 958–962(1989) and Saunders, *Clinical Chemistry*, 37(9): 1531–3(1991). The suspension is then removed for analysis and the process is repeated as many times as necessary to produce a number of fractions each corresponding to a different age of RBC cohorts. Typically, three or more fractions are obtained. The preferred number of fractions is ten.

Figure 1:
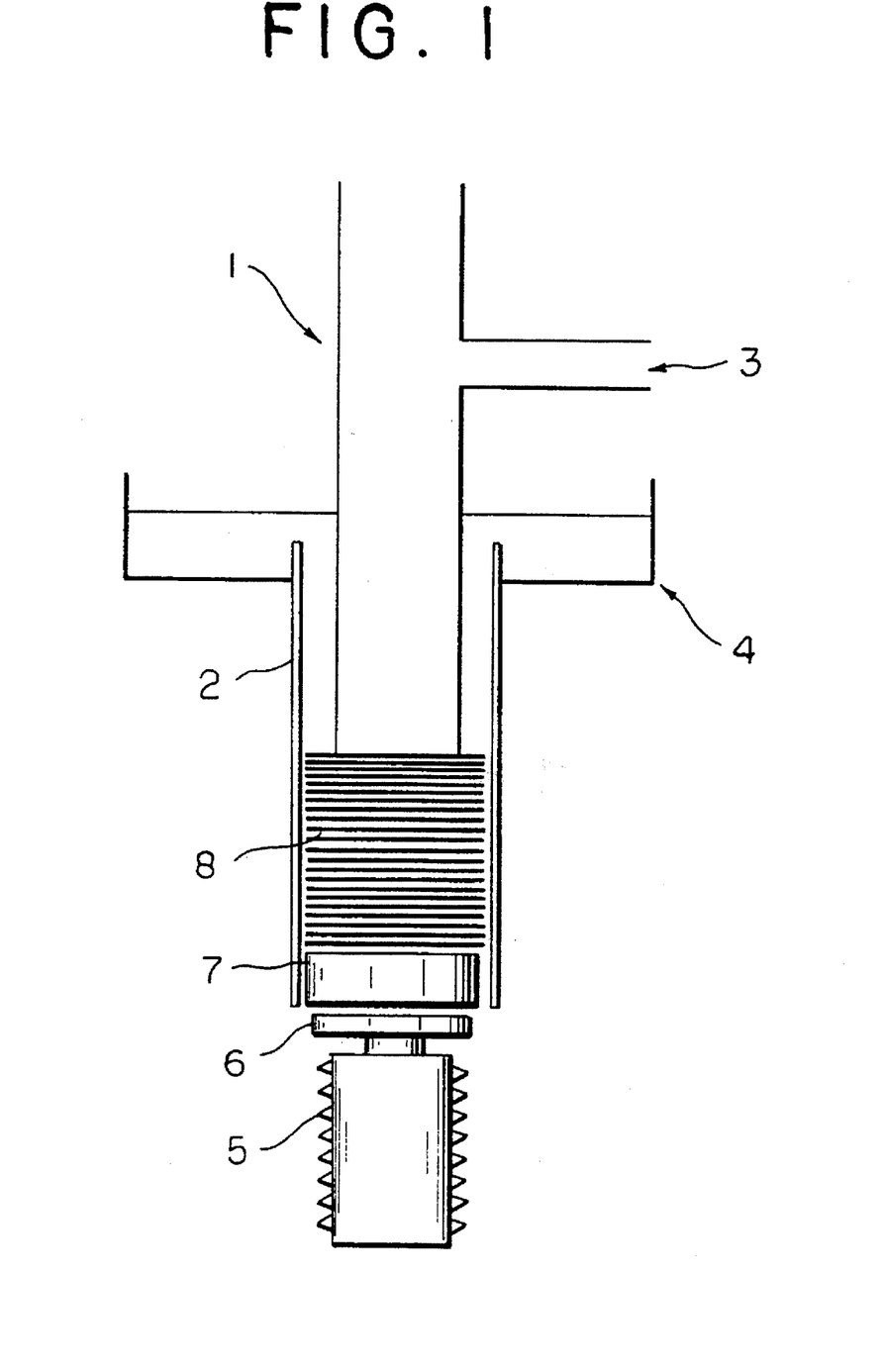
The Figure shows a suction probe for sequentially harvesting by age cohorts of red blood cells from a blood sample.

One preferred method for removing red blood cells from the pack is to pump them off with a suction device, as shown in FIG. 1. The suction device 1 used is lowered into a centrifuged capillary tube 2 until just above the surface of the contents of the capillary tube 2. The outer diameter of the suction device 1 is slightly less than the internal diameter of the capillary tube 2. The space between them should be sufficient to permit a liquid to travel between them. Alternatively, one or preferably several grooves may be located around the suction device 1 part of the way down, but not as far down as the tip of the device, to permit fluid to pass between the suction device 1 and the capillary tube 2. Air or other gas inert to red blood cells may be added to the suctioned flow of red blood cells and liquid through a side port 3 to form a gas bubble in the flowing stream in order to provide further separation of red blood cell age cohorts. The gas flow may also be modified to adjust the suction effect of the suction device 1.

A supply of liquid, of a pH and salt concentration acceptable to red blood cells, is provided to the space between the capillary tube 2 and the suction device 1 by suitable means 4. One good liquid is phosphate buffered saline (PBS). This liquid suspends the red blood cells as it washes away a thin surface layer of the red blood cell pack and permits the top fraction to be withdrawn by the suction device 1 without significant damage. As the suction device 1 is lowered, successive layers of packed red blood cells are removed. The suction tube may be connected to a peristaltic pump to effect constant pressure and may also be coupled with pumping a liquid such as PBS into any suitable means for delivering liquid. As an alternative to lowering the suction device, the entire capillary tube may be raised. One convenient mechanism is through an advancing screw 5 which can be slowly rotated to advance the tube upwards. A swivel 6 or lubricant may be placed between the advancing screw and the capillary tube lower plug 7. This permits minimal disruption of the red blood cell pack while gradually raising the capillary tube. Alternatively, the capillary tube may be clamped in position and the plug 7 pushed through the capillary tube 2 to force the pack of red blood cells 8 upwards. This option may be used without the suction device if so desired. However, more carry over is observed by this alternative and this reduces effective harvesting of density layers.

The fractions of red blood cells may be deposited into separate containers or optionally mixed with reagents and run sequentially in any analytical system if so desired. Among the preferred assays to perform are those relating to the modification of hemoglobin such as the glycosylation mentioned previously to determine a history of hemoglobin glycosylation rates, and therefore obtain a history of blood glucose levels. Enzymes may also be assayed; pyruvate kinase slowly decreases in activity with increasing age of the erythrocyte, Seeman et al, *American Journal of Hematology*, 8:31–41(1980). Other cell types, such as the proportion of reticulocytes, may also be measured to determine blood turnover.

The effectiveness of diabetic therapies may be determined by observing the plots generated by measuring glycohemoglobin in each age fraction of red blood cells. Examples of four different results are shown in Saunders, *Clinical Chemistry*, 37(9): 1531–3 (1991) in FIG. 1.

EXAMPLE

Glass capillary tubes were obtained from Scientific Products catalogue B4416–10, P5214–5, Drummond (Wiretrol), Becton Dickinson Primary Care Division glass tubes as used for QBC, and Safetec microhematocrit tubes. All capillary tubes were cleaned by soaking in sodium hydroxide saturated ethanol for fifteen minutes. The tubes were then coated internally by one of the following methods:

1. Three to five tubes were connected in series with sections of tightly fitting plastic tubing (Tygon) and the last tube in the series was connected to a Pasteur pipette. Ethanol without sodium hydroxide was drawn back and forth through the tubes ten times to wash out the residual sodium hydroxide. Then chloroform was drawn back and forth through the tubes to remove any residual ethanol. A solution of 1% polystyrene in chloroform was drawn back and forth through the tubes eight to ten times and then expelled from the tubes using air pressure. The tubes were separated, dried on a hot plate at 40° C., washed with ethanol and dried again.

2. The same steps were performed as above except that alternating air bubbles at one second intervals until about five milliliters of each solvent or solution was drawn through the tube. This method uses a one directional peristaltic pump.

3. The same steps were performed as above except for substituting Teflon, a fluoro-aliphatic resin in 1,1,1-trichloroethane (Scotch-Gard), or 1% polyvinylpyrrolidone in water for the polystyrene.

4. Other constituents and solvents have also been used. For example, polyethylene dissolved in chloroform gradually over many days. The concentration in this case is not precisely determined.

Blood was mixed with EDTA, a standard anticoagulant and capillary tubes were filled to within 2 mm of the top with samples of the blood. The bottom end was sealed with clay, as usually done for microhematocrit determination. The tubes were topped with Fluorinert (Sigma Chemicals) and then centrifuged in a standard Microhematocrit centrifuge (Adams) at a combination of 900 RPM (80×G) for five minutes, then 7200 RPM (4000×G) for 20 minutes and finally at 12,000 RPM (11,000×G) for five minutes.

The suction device as depicted in the figure was used to separate various fractions of red blood cells. The fractions were tested for glycohemoglobin using the methods described in Saunders, *Clinical Chemistry*, 37(9): 1531–3 (1991) and the pyruvate kinase activity was measured by the method of Seaman et al, *American Journal of Hematology*, 8: 31–41 (1980). Blood samples were generally less than 90 minutes old when used as baseline controls. In the data below, the baseline results were held constant and the effects of changing one or more variables are given with respect to that baseline.

The first experiment compared the results between plastic capillary tubes and glass capillarey tubes.

The second experiment compared the effects of sample age on the results.

The third experiment compared the effects of various centrifugal forces.

The fourth experiment set compared the effects of an internal coating on the glass capillary. Two such experiments were conducted.

The fifth experiment compared the effects on deformability by using different chemical means for altering red blood cell membranes.

With the base line control showing a gradual slope, all other readings are given in comparison. The Table 1 presents the possible result options:

TABLE 1

Summary of Results from Experiments 1, 2 and 4.

| Time | Polyethylene Capillary | Glass Capillary | Glass Capillary 1% Polystyrene |
|---|---|---|---|
| Fresh | Baseline Condition | 4a | 0a |
| 3 hours | 0a | 4a | 0a |
| 24 hours | 0a | 4a | 0a |
| 48 hours | 0a | 4a | 0b |
| 72 hours | 0a | 4a/4c | 0b |
| 1 week | 0a | 4c | 0b |
| 2 weeks | 0a | 4c | 0b |

0 no change in slope
1 steeper overall slope
2 steeper slope in less dense cells
3 steeper slope in more dense cells
4 shallower overall slope
5 shallower slope in less dense cells
6 shallower slope in more dense cells
a no change in regularity
b more regular increments
c less regular increments The results for experiment 1 demonstrated that when one replaces plastic with glass capillary tubes one observes a shallower overall slope without change in the regularity. This gives a result of 4a.

For the second experiment, whole blood samples with standard EDTA anti-coagulant were held at refrigerator temperatures for various periods of times and the standard conditions for centrifugation were applied. The capillary tubes were polyethylene or plain glass or 1% polystyrene treated glass. These results are also displayed in Table 1.

The results from various changes in the centrifugal force are displayed in Table 2 relative to each other. The experimental conditions are based on the baseline conditions with the following changes. The duration of each step on the baseline is 5 minutes, 20 minutes and 5 minutes respectively.

TABLE 2

Study of Separate Effects of Different Forces in Cell Separation.

| 80 × G, 4000 × G, and 11000 × G | baseline |
|---|---|
| omit 80 × G | 4a |
| omit 4000 × G | 4c |
| omit 11000 × G | 1b |
| double time 80 × G | 1b |
| double time 4000 × G | 1a |
| double time 11000 × G | 1b |
| continuous linear RPM change | 4a |
| seven speed incremental doubling | 4c |

*Starting at 155 RPM and increasing 300 RPM/minute for 35 minutes, reaching 12,000 RPM
**Seven consecutive steps of 5 minutes each as follows: 1500, 2120, 3000, 4240, 6000, 8500, 12,000 RPM In Table 2, double time means replacing a 5 minute spin with a 10 minute spin, or 20 minutes with 40 minutes.

"Continuous linear RPM change" means starting at the (slow) inertial speed of the centrifuge, 1500 RPM, and gradually increasing the RPM at 300 RPM/minute until 12,000 RPM is reached in 35 minutes.

"Seven speed incremental doubling" means seven consecutive 5 minute intervals at 1500, 2120, 2000, 4242, 6000, 8500 and 12,000 RPM.

Certain inconsistencies in these results may be due to differences in the age of the samples. However, the trend is demonstrated that each of the three centrifugations contributes improvement in slope and/or consistency of glycohemoglobin concentration results from one fraction to the next. However, increasing the number of increments or using a continuous change in RPM did not improve the results.

As a more detailed study of the intermediate forces, a set of more closely space RPM centrifugations of five minutes each were substituted for the 4000×G (7200 RPM) 20 minute component, while retaining the 80×G and 11,000×G components as before. Each of the intermediate components was also experimentally deleted or its time doubled, while holding the remainder constant. The experiment was run after the sample was 24 hours past removal from the patient.

This protocol is depicted in Table 3

TABLE 3

More Detailed Study of Mid Range G Forces on Cell Separation

| RMP | Times of Centrifuging in Minutes | | | | | | | |
|---|---|---|---|---|---|---|---|---|
| 2400 | 5 | 0 | 5 | 5 | 5 | 10 | 5 | 5 |
| 3600 | 5 | 5 | 0 | 5 | 5 | 5 | 10 | 5 | 5 |
| 5800 | 5 | 5 | 5 | 0 | 5 | 5 | 5 | 10 | 5 |
| 7200 | 5 | 5 | 5 | 5 | 0 | 5 | 5 | 5 | 10 |
| Results: | (Baseline) | 0a | 0a | 6c | 4c | 0c | 4a | 1a | 1b |

Each result is the composite of two complete experimental runs. These results are interpreted to mean that the stronger forces have a greater influence in both slope and consistency of increments between fractions.

Various internal coatings were used on glass capillary tubes. For this experiment, the capillary was first cleaned by applying a solution of 1% sodium hydroxide in ethanol for five minutes, followed by three rinses in absolute ethanol.

The substance applied was dissolved at specified concentration and specified solvent as listed below. Subsequently, negative pressure was applied to the capillary to remove excess liquid, and then the capillary was dried on a hot plate. The results are shown in Table 4.

TABLE 4

| | Cleaning | polyvinyl pyrrolidone | poly-ethylene | poly-styrene | siliconizing or fluorosil |
|---|---|---|---|---|---|
| a) baseline = 0a | | | | | |
| b) No treatment = 4c | | | | | |
| c) Clean only | X = 1a | | | | |
| d) | | 1% = 1a | | | |
| e) | | | 1% = 1b | | |
| f) | | | | .1% = 1a | |
| g) | | | | .3% = 1a | |
| h) | | | | 1.0% = 1b | |
| i) | | | | 3.0% = 1b | |
| j) | | | | 5.0% = 3b | |
| k) | | | | | 1% = 1b |

The siliconizing experiment was performed by extrusion, and demonstrates an effect of reducing carry over, as cells may stick to the capillary wall during extrusions. Repeat of this experiment where harvesting is by suction is summarized as follows:

| a) No coating | 4c |
|---|---|
| b) 1% polystyrene | 0a |
| c) siliconized tube | 6c |
| d) fluorosiliconized tube | 4c |

An experiment was conducted to demonstrate the effect of improving deformability of the red blood cells. In this experiment, the baseline was a microhematocrit capillary which was not pre-treated. The experiment was performed with both untreated and polystyrene 1% pre-treated capillaries at standard 180, 7200 and 14,000×G routine.

For this experiment, whole blood samples were pre-incubated with one of several biologically active agents with specific concentration and results as indicated in Table 5.

TABLE 5

| | Treatment by incubation | |
|---|---|---|
| | chlorpromazine | taurocholate |
| a) Baseline = 0a | | |
| b) | 5 microM = 1a | |
| c) | 10 microM = 1c | |
| d) | 20 microM = oc | |
| e) | | 0.25 mM = 1a |
| f) | | 0.50 mM = 0a |

Pre-incubations with chlorpromazine or taurocholate or a combination thereof, in the absence of an internal coating, was done to see if increasing cell deformability accounts for the working of the present invention. It was found that cell deformability alone is not sufficient to provide the separation needed for compiling an accurate history, because the effect was less than with the polystyrene coating. Combining chlorpromazine with polystyrene coating exhibited only a minor improvement over polystyrene alone.

In a further study, the effects of polystyrene and chlorpromazine were separately evaluated with the following findings:

| | |
|---|---|
| a) No polystyrene, no chlorpromazine | 6c |
| b) No polystyrene, 5 μM chlorpromazine | 1a |
| c) No polystyrene, 10 μM chlorpromazine | 2a |
| d) 1% polystyrene, no chlorpromazine | 1b |
| e) Polyethylene capillary | 0a (baseline) |
| f) polyethylene capillary, 5 μM chlorpromazine | 1b |

However, note that e) was performed several times as a baseline for different samples used in this experiment, as f) was conducted on a sample different from the one used for a)–d).

This experiment also provides evidence that chlorpromazine acts independently of polystyrene, but that polystyrene may provide the greater of the two effects.

A comparative experiment was conducted to compare separation of red blood cells by centrifugation using tubes comprising a polyethylene liner enclosed in a rigid metal sheath. For this experiment, only the centrifugation was varied.

(1) The baseline condition was three steps: at 80×G for five minutes, 7200×G for 15 minutes, and 12,000×G for 5 minutes.

(2) Example A comprised centrifugation at 12,000G 5 for five minutes.

(3) Example B comprised centrifugation at 2000G for five minutes and 1000×G for an additional ten minutes.

(4) Example C pre-incubated the sample with hypotonic solution, and then centrifuged at 80×G for five minutes, 7200×G for 15 minutes, and 12,000×G for 5 minutes.

The results are shown in Table 6:

TABLE 6

| | |
|---|---|
| Baseline | 0a |
| Example A | 5c |
| Example B | 6c |
| Example C | 2a |

It was found that the slower initial spins of the baseline condition do contribute to separation by density. However, the higher G forces are required to complete the separation. If the higher G forces are not supplied, there are less dense cells trapped far down in the capillary tube. Indeed, in this case, some of the lowest layers had lower GHb than any other, and the order is almost random when the entire sample is considered.

Hypotonic conditions were found to contribute to even better separation, particularly for the lightest layers.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

What is claimed is:

1. A method of sorting red blood cells substantially according to their densities into at least three separate fractions, which comprises (a) placing red blood cells of different densities into a centrifuge tube means, (b) centrifuging said cells until they are sorted substantially according to their density, and (c) recovering at least three separate fractions, each fraction having a different average density, from said sorted cells, where the centrifuge tube means comprises a tube which is capable of withstanding forces applied during centrifugation, said tube being formed of a material which is not a plastic, said tube having an inner surface coating of a water-insoluble plastic, such that the degree of density sorting is greater than that which would have been achieved under the same conditions in the absence of said inner surface coating.

2. The method of claim 1 wherein the centrifuging is conducted in the absence of an artificial density gradient medium.

3. The method of claim 1 wherein red blood cells are sorted substantially according to their age, said method comprising:

(a) sorting red blood cells substantially according to their density by the method of claim 1, and recovering the cells in sorted order so as to obtain at least three fractions of different average densities, and (b) correlating the average density of each fraction with the average age of the cells.

4. The method of claim 1 wherein the coating is not a copolymer of polyvinylpyrrolidone and vinyl acetate.

5. The method of claim 1 wherein the coating is an organic polymer.

6. The method of claim 1 in which the cells are sorted into at least ten separate fractions.

7. The method of claim 1 wherein the water-insoluble plastic is selected from the group consisting of polyolefins, polystyrenes; halogenated polymers; water-insoluble poly vinylalcohols; polyethyleneglycols and fatty acid esters thereof; polycarbonates; polyesters; synthetic rubbers, thermosetting resins; polyamides; polyacetals; acrylic resins, including acrylic and methacrylic esters and copolymers thereof; ionomer resins; poly aryl sulfones; and mixtures and copolymers thereof.

8. The method of claim 1 wherein the plastic is polystyrene.

9. The method of claim 1 wherein the red blood cells are pretreated with a chemical deformation agent to increase deformability of individual cells with altering their relative density.

10. The method of claim 9 wherein the chemical deformation agent is chlorpromazine.

11. The method of claim 1 wherein an additive is added to soften the red blood cell membranes.

12. The method of claim 11 wherein the additive is taurocholate.

13. The method of claim 11 wherein the additive is chlorpromazine.

14. The method of claim 1 wherein step (b) comprises:
centrifuging for a first predetermined period of time at a first constant predetermined centrifugal force, and
centrifuging for a second predetermined period of time at a second and greater constant predetermined centrifugal force.

15. The method according to claim 14 further comprising centrifuging said cells for a third predetermined period of time at a third and greater predetermined centrifugal force.

16. The method of claim 15 wherein the red blood cells are centrifuged (a) at a force of about 20 to about 200 G for about five minutes, (b) at about 2,000 to about 6,000 G for about twenty minutes, and (c) at greater than about 8,000 G for about five minutes.

17. The method of claim 16 wherein force (a) is about 80 G, force (b) is about 4,000 G, and force (c) is about 11,000 G.

18. A method for producing at least three separate fractions of red blood cells, each fraction having a different average density, which comprises
(a) sorting the red blood cells, substantially in order of their densities, by the method of claim 1, the red blood cells forming a pack definable into a plurality of layers of different average densities, wherein the red blood cells of lowest density form the surface layer of the pack, and cells of greater density form progressively deeper layers of the pack, and
(b) removing the surface layer of red blood cells from the pack, by suction, without disturbing the other layers of the pack, so that the next layer becomes the new surface layer, and repeating step (b) until at least three separate fractions of different average densities have been collected.

19. The method of claim 18 wherein the tube material is glass.

20. The method of claim 19 wherein the centrifuge tube means is a glass capillary tube with an inner surface coating of a water-insoluble plastic.

21. A method for producing at least three fractions of red blood cells of different densities comprising:
centrifuging red blood cells in a centrifuge tube means into a pack ordered substantially according to their density;
immobilizing said red blood cells while said red blood cells are in said centrifuge tube means; and
sequentially removing surface layers of red blood cells from the pack of red blood cells without disturbing the other layers in the pack.

22. The method according to claim 21 wherein said red blood cells are immobilized by freezing.

23. A method for ordered red blood cells substantially according to their density which comprises:
pretreating whole blood with at least one chemical agent means to exaggerate differences in density and increase the deformability of the individual cells without altering their relative density;
centrifuging the cells until they are ordered according to density.

24. The method according to claim 23 wherein said chemical agent is chlorpromazine in water.

* * * * *